(12) United States Patent
Swift et al.

(10) Patent No.: US 7,169,748 B2
(45) Date of Patent: Jan. 30, 2007

(54) FRAGRANCE COMPOUNDS

(75) Inventors: Karl Andrew Dean Swift, Kent (GB); Kim Joyce Yarwood, Kent (GB)

(73) Assignee: Quest International Services B.V., Naarden (NL)

( * ) Notice: Subject to any disclaimer, the term of this patent is extended or adjusted under 35 U.S.C. 154(b) by 0 days.

(21) Appl. No.: 10/481,452

(22) PCT Filed: Jun. 10, 2002

(86) PCT No.: PCT/GB02/02655

§ 371 (c)(1), (2), (4) Date: Dec. 19, 2003

(87) PCT Pub. No.: WO03/000648

PCT Pub. Date: Jan. 3, 2003

(65) Prior Publication Data

US 2004/0157765 A1    Aug. 12, 2004

(30) Foreign Application Priority Data

Jun. 25, 2001 (EP) .................................. 01305505

(51) Int. Cl.
*A61Q 13/00* (2006.01)
(52) U.S. Cl. ............................ 512/21; 512/20; 512/25; 512/26; 564/223
(58) Field of Classification Search ............... 512/21, 512/20, 25, 26; 564/223
See application file for complete search history.

(56) References Cited

U.S. PATENT DOCUMENTS 3,909,462 A    9/1975 Gubler
4,666,943 A *  5/1987 Noguchi et al. ............ 514/627
5,856,295 A *  1/1999 Sell ............................. 512/21

FOREIGN PATENT DOCUMENTS

WO    WO 96/30470 A    10/1996
WO    WO 99/18926 A    4/1999

OTHER PUBLICATIONS

T. H. Siddall, et al.: "Geminal Proton Nonequivalences and Related Phenomena in Some N-Substituted Amides" Journal of the American Chemical Society., vol. 88, No. 6, Mar. 20, 1996, pp. 1172-1176, XP002183408 ISSN: 0002-7863.

* cited by examiner

*Primary Examiner*—Monique T. Cole
(74) *Attorney, Agent, or Firm*—Morgan Lewis & Bockius LLP

(57) ABSTRACT

Novel compounds having the structure (I) where R=methyl, ethyl or propyl, $R_1$=methyl or H, $R_2$=methyl, ethyl or propyl, $R_3$=methyl or H, $R_4$=methyl or ethyl, $R_5$=H or methyl, and where $R_3$ and $R_5$ are not both H, excluding N-ethyl-2-methyl-N-(3-methylphenyl) propanamide, can have desirable odour properties, typically of a tropical fruit, cassis character and find use in perfumes and perfumed products

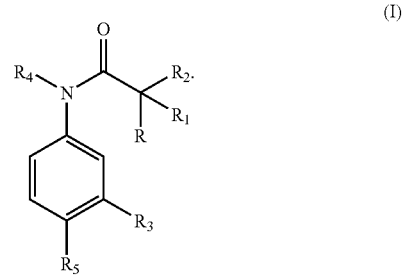

(I)

7 Claims, No Drawings

FRAGRANCE COMPOUNDS

FIELD OF THE INVENTION

This invention concerns novel fragrance compounds, and perfumes and perfumed products comprising the novel compounds.

BACKGROUND TO THE INVENTION

Siddall T. H. et al, Journal of the American Chemical Society, 1966, 88(6), p1172–1176 describes the preparation, and more particularly the analysis by proton magnetic resonance (pmr) spectroscopy, of a number of N,N-disubstituted amides.

The present invention concerns novel N,N-disubstituted amides, particularly those amides possessing desirable fragrance properties.

SUMMARY OF THE INVENTION

In one aspect the present invention provides a compound having the structure

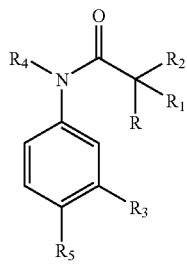

where R=methyl, ethyl or propyl, $R_1$=methyl or H, $R_2$=methyl, ethyl or propyl, $R_3$=methyl or H, $R_4$=methyl or ethyl, $R_5$=H or methyl, and where $R_3$ and $R_5$ are not both H, excluding N-ethyl-2-methyl-N-(3-methylphenyl)propanamide.

For brevity and simplicity, such materials will be referred to as "the amide", "the novel amide" or "the amide of the invention".

The amides of the invention can possess fragrance or odour properties which are generally regarded as interesting, pleasant or attractive, typically having fruity, cassis odour properties.

The currently preferred amide in accordance with the invention has R=ethyl, $R_1$=H, $R_2$=ethyl, $R_3$=methyl, $R_4$=methyl and $R_5$=H. This compound thus has the structure

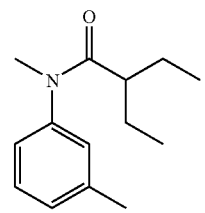

and is 2-ethyl-N-methyl-N-(3-methylphenyl)butanamide. For brevity and simplicity this amide is referred to herein as compound 1. Compound 1 has desirable odour properties, generally described as tropical fruit, cassis. Compound 1 has a wide range of chemical stability and so finds potential use in a wide range of products. Compound 1 also has excellent insect repellency properties, equivalent to those of N-N-diethyl-m-toluamide (DET). Furthermore, compound 1 has good cloth and hair substantivity properties, having good substantivity on wet cloth and moderate substantivity on dry cloth.

Compound 1 might be considered to have some structural similarities to the following known fragrance molecules:

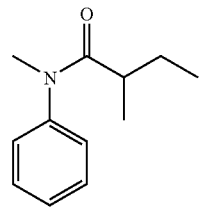

A

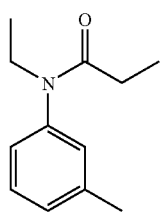

B

Molecule A is known by the Trade Mark Gardamide and has grapefruit, rhubarb odour properties. Molecule B (described in WO 96/30470 of Quest) is known by the Trade Mark Agarbois and has precious wood odour properties. It should thus be noted that the odour profile of compound 1 (tropical fruit, cassis) is very different from those of molecules A and B, in a way that is not predictable. Further, compound 1 is far superior to molecules A and B in terms of additional benefits such as better substantivity properties (both wet and dry cloth substantivity of compound 1 are better than that of molecules A and B). Moreover, the insect repellent properties of compound 1 are superior to those of molecules A and B.

Further, amides in accordance with the present invention, and particularly compound 1, might also be considered to have some structural similarities to the molecule, N-phenyl-N-methyl-2-ethylbutyric acid amide which is described in U.S. Pat. No. 3,909,462 as being useful in perfumery on the basis of its herby note. The molecule is also described as possessing a grapefruit aroma. Both of the odour/aroma descriptors given for this molecule are different to the odour properties of compound 1.

A further amide exemplifying the invention has R=methyl, $R_1$=H, $R_2$=propyl, $R_3$=methyl, $R_4$=methyl and $R_5$=H. This compound thus has the structure:

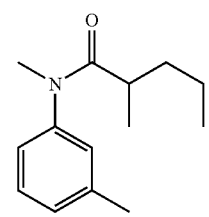

and is N, 2-dimethyl-N-(3-methylphenyl)pentanamide. This amide has fruity, cassis, citrus odour properties.

The odour properties of the amides of the invention mean that an amide or mixture of amides in accordance with the invention may be used as such to impart, strengthen or improve the odour of a wide variety of products, or may be used as a component of a perfume (or fragrance composition) to contribute its odour character to the overall odour of such perfume. For the purposes of this invention a perfume is intended to mean a mixture of fragrance materials, if desired mixed with or dissolved in a suitable solvent or mixed with a solid substrate, which is used to impart a desired odour to the skin and/or product for which an agreeable odour is indispensable or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc. As noted above, amides in accordance with the invention can show good substantivity to hair and cloth, both wet and dry, and hence have good potential for use in fabric treatment products and hair care products.

Other fragrance materials which can be advantageously combined with one or more amides according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic, and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with one or more amides according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, α-hexylcinnamaldehyde, 2-methyl-3-(p-tert-butylphenyl) propanal, 2-methyl-3-(p-isopropylphenyl)propanal, 2-(p-tert-butylphenyl)-propanal, 2,4-dimethyl-cyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

Solvents which can be used for perfumes which contain an amide according to the invention are, for example: ethanol, isopropanol, diethyleneglycol monoethyl ether, dipropylene glycol, diethyl phthalate, triethyl citrate, isopropyl myristate, etc.

The quantities in which one or more amides according to the invention can be used in perfumes or in products to be perfumed may vary within wide limits and depend, inter alia, on the nature of the product, on the nature and the quantity of the other components of the perfume in which the amide is used and on the olfactive effect desired. It is therefore only possible to specify wide limits, which, however, provide sufficient information for the specialist in the art to be able to use an amide according to the invention for his specific purpose. Typically, a perfume comprises one or more amides in accordance with the invention in an olfactively effective amount. In perfumes an amount of 0.01% by weight or more of an amide according to the invention will generally have a clearly perceptible olfactive effect. Preferably the amount is 0.1 to 80% by weight, more preferably at least 1%. The amount of the amide according to the invention present in products will generally be at least 10 ppm by weight, preferably at least 100 ppm, more preferably at least 1000 ppm. However, levels of up to about 20% by weight may be used in particular cases, depending on the product to be perfumed.

In a further aspect the invention provides a perfume comprising one or more amides of the invention in an olfactively effective amount.

The invention also covers a perfumed product comprising one or more amides of the invention.

Amides in accordance with the invention may be readily synthesised, potentially cheaply, from the corresponding amine by reaction with an appropriate acid chloride or anhydride.

The invention will be further described, by way of illustration, in the following Examples.

EXAMPLE 1

This example describes synthesis of 2-ethyl-N-methyl-N-(3-methylphenyl)butanamide (compound 1) by the following route:

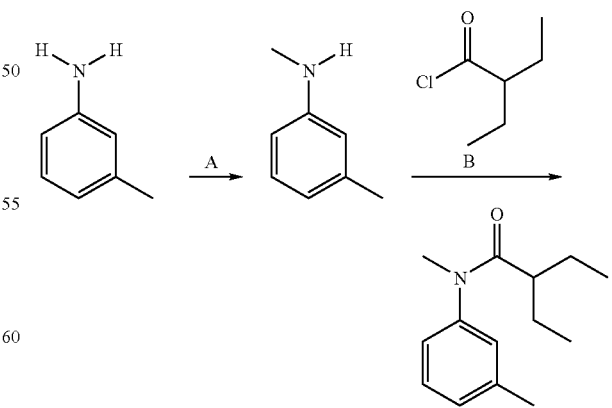

Preliminary step A is only used when N-methyl-m-toluamide is not available, and is as described in Org. Synth. Coll. Vol. IV (1963), p420.

Step B (via the acid chloride) uses the following materials:

| | |
|---|---|
| N-methyl-m-toluamide | 121 g, 1.0 mol |
| Ethylbutyryl chloride | 152 ml, 1.1 mol |
| Triethylamide | 167 ml, 1.2 mol |
| Dichloromethane | 1000 ml |

The acid chloride was added to a stirred solution of the N-methyl-m-toluamide in dichloromethane whilst keeping the temperature below 20° C. Once the addition was complete the reaction was left to warm up to room temperature and then poured into water (500 ml). The organic and aqueous layers were thoroughly mixed by shaking and once separated the aqueous layer was discarded. The organic phase was washed with a further 500 ml portion of water, and then dried with magnesium sulphate.

The solvent (and residual triethylamine) was removed under vacuum and the crude product (200 g) that remained was distilled under reduced pressure (101° C.@0.25 mmHg) to yield a colourless liquid. The product was stirred with activated charcoal for 24 hours followed by filtration through celite.

After the charcoal treatment 162 g (74%) of material with the desired odour quality (tropical fruit, cassis) was obtained.

$^1$H NMR (400 MHz, CDCl$_3$, Ref TMS at 0.0 ppm) 7.25 (1H), 7.10 (1H), 6.91 (2H), 3.25 (3H), 2.35 (3H), 2.15 (1H), 1.58 (2H), 1.31 (2H), 0.75 (6H) $^{13}$C NMR (100 MHz, CDCl$_3$, Ref. CDCl$_3$ at 77.0 ppm) 176.2, 144.2, 139.7, 129.4, 128.5, 128.4, 124.9, 45.0, 37.4, 26.1, 21.3, 12.2

EXAMPLE 2

A perfume in accordance with the invention was prepared by mixing together the following materials.

| | % by weight |
|---|---|
| Aquanal (Q) | 1 |
| Bangalol (Q) | 5 |
| Bergamot AB 1589 | 5 |
| Cervolide (Q) | 25 |
| Citronellol Pure | 0.5 |
| Dipropylene Glycol | 20.5 |
| Ethyl acetoacetate | 1 |
| Geranium Bourbon Pure | 0.5 |
| Ionone (Q) | 1 |
| Ligustral (Q) 10% solution in DPG | 1.5 |
| Magnolan (H & R) | 5 |
| Tropical Fruit Amide (compound 1) | 1 |
| Maltol 10% solution in DPG | 0.5 |
| Methyl dihydrojasmonate high Cis 70 (Q) | 12 |
| Methyl pamplemousse (G) | 0.5 |
| Nerolidol | 5 |
| Orange Brazil Pure | 2 |
| Orange Flower AB 2169 | 0.5 |
| Peomosa (IFF) | 2.5 |
| Rhubofix (F) 10% solution in DPG | 2 |
| Rose Oxide Racemic 1% solution in DPG | 1 |

-continued

| | % by weight |
|---|---|
| Silvanone (Q) | 5 |
| Veloutone (F) 10% solution in DPG | 2 |

DPG = Dipropylene glycol
Q, H & R, F, IFF and G are all abbreviations for company names (Q = Quest, H & R = Haarman & Reimer, F = Firmenich, IFF = International Flavours and Fragrances, G = Givaudan) and the associated materials are identified by Trade Marks.

The invention claimed is:
1. A compound having the structure

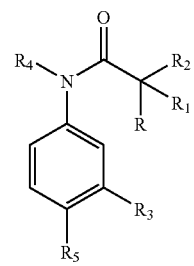

wherein R=methyl, ethyl or propyl, R$_1$=methyl or H, R$_2$=methyl, ethyl or propyl, R$_3$=methyl or H, R$_4$=methyl or ethyl, R$_5$=H or methyl, and where R$_3$ and R$_5$ are not both H, excluding N-ethyl-2-methyl-N-(3-methylphenyl)propanamide, said compound being characterized by its fruity cassis odor.

2. A compound according to claim 1, having the structure

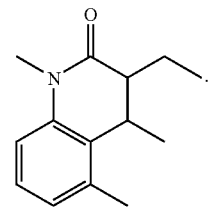

3. A compound according to claim 1, having the structure

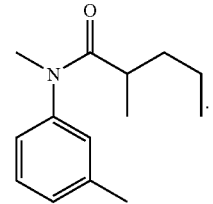

4. A perfume comprising one or more compounds in accordance with claim 1, in an olfactively effective amount.
5. A perfume according to claim 4, wherein the compound is present in an amount of at least 0.01% by weight.
6. A perfume according to claim 5, wherein the compound is present in an amount in the range 0.1 to 80% by weight.
7. A perfumed product comprising one or more compounds according to claim 1 or a perfume according to claim 4.

* * * * *

UNITED STATES PATENT AND TRADEMARK OFFICE
CERTIFICATE OF CORRECTION

PATENT NO. : 7,169,748 B2
APPLICATION NO. : 10/481452
DATED : January 30, 2007
INVENTOR(S) : Karl Andrew Dean Swift et al.

It is certified that error appears in the above-identified patent and that said Letters Patent is hereby corrected as shown below:

Column 6, lines 35-44, the structure in claim 2 is corrected to read as follows:

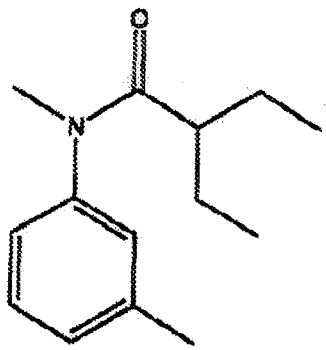

Signed and Sealed this

Thirtieth Day of November, 2010

David J. Kappos
*Director of the United States Patent and Trademark Office*